United States Patent [19]

Buchanan et al.

[11] Patent Number: 5,153,931
[45] Date of Patent: Oct. 6, 1992

[54] FIBER OPTIC HYDROGEN SENSOR

[76] Inventors: Bruce R. Buchanan, 1985 Willis, Batesburg, S.C. 29006; William S. Prather, 2419 Dickey Rd., Augusta, Ga. 30906

[21] Appl. No.: 678,520

[22] Filed: Apr. 1, 1991

[51] Int. Cl.$^5$ ............................................... G02B 6/02
[52] U.S. Cl. ...................................... 385/12; 385/144; 385/123
[58] Field of Search ................. 350/96.29, 96.3, 96.34; 356/51; 250/227.18; 385/144, 123, 12

[56] References Cited

U.S. PATENT DOCUMENTS

| | | | |
|---|---|---|---|
| 3,998,591 | 12/1976 | Eckfeldt | 23/253 |
| 4,661,320 | 4/1987 | Ito et al. | 422/86 |
| 4,668,635 | 5/1987 | Forster | 436/134 |
| 4,718,747 | 1/1988 | Bianchi et al. | 385/144 |
| 4,763,009 | 8/1988 | Février et al. | 250/227.18 X |
| 4,764,343 | 8/1988 | Nyberg | 422/83 |
| 4,824,789 | 4/1989 | Yafuso et al. | 436/68 |
| 4,834,497 | 5/1989 | Angel | 350/96.29 |
| 4,849,172 | 7/1989 | Yafuso et al. | 422/55 |
| 4,861,727 | 8/1989 | Hauenstein et al. | 436/136 |
| 4,927,768 | 5/1990 | Coughlin et al. | 436/172 |
| 4,929,049 | 5/1990 | Le Goullon | 385/12 |
| 4,954,318 | 9/1990 | Yafuso et al. | 350/96.29 X |
| 5,006,314 | 4/1991 | Gourley et al. | 350/96.29 X |
| 5,026,139 | 6/1991 | Klainer et al. | 385/12 |

Primary Examiner—John D. Lee
Assistant Examiner—S. W. Barns
Attorney, Agent, or Firm—Harold M. Dixon; William R. Moser; Richard E. Constant

[57] ABSTRACT

An apparatus and method for detecting a chemical substance by exposing an optic fiber having a core and a cladding to the chemical substance so that the chemical substance can be adsorbed onto the surface of the cladding. The optic fiber is coiled inside a container having a pair of valves for controlling the entrance and exit of the substance. Light from a light source is received by one end of the optic fiber, preferably external to the container, and carried by the core of the fiber. Adsorbed substance changes the transmissivity of the fiber as measured by a spectrophotometer at the other end, also preferably external to the container. Hydrogen is detected by the absorption of infrared light carried by an optic fiber with a silica cladding. Since the adsorption is reversible, a sensor according to the present invention can be used repeatedly. Multiple positions in a process system can be monitored using a single container that can be connected to each location to be monitored so that a sample can be obtained for measurement, or, alternatively, containers can be placed near each position and the optic fibers carrying the partially-absorbed light can be multiplexed for rapid sequential reading by a single spectrophotometer.

18 Claims, 2 Drawing Sheets

FIBER OPTIC HYDROGEN SENSOR

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

This invention relates to an apparatus for determining the concentration of a chemical substance in a gas. More particularly, the invention relates to a system determining the concentration of hydrogen in a gas by adsorbing hydrogen onto a light-carrying optic fiber and measuring the change in light transmitted through the fiber.

2. Discussion of Background

Apparatus for detecting and measuring the concentration of specific chemicals in gases have various applications, including, detection of toxic or explosive gases in the atmosphere, monitoring the constituents in industrial process streams and detection of contaminants in ground water. There are many different apparatus for such purposes, responding to electrical, chemical or optical effects induced by the presence of the chemical substance in the carrying fluid.

Each type of detector has characteristics that are advantageous for some uses and inappropriate for others. Detectors which depend on electrical effects may be influenced adversely by electromagnetic interference. Electronic detectors can also be hazardous if used for the detection of substances in flammable or explosive gases because of the risk of ignition.

Another method for detecting chemical constituents, gas chromatography, is somewhat time consuming and costly, requiring elaborate handling procedures for the sample and trained technicians to operating the gas chromatograph.

Some types of detectors can become contaminated by other constituents that interfere with the reactive portion of the sensor preventing accurate measurements. Most detectors are poisoned by nitric oxide, for example, a gas generated as a by-product of many of the processes which generate hydrogen. In many cases this pollutant results in complete failure of the detector.

Another disadvantage of the existing detectors is limited monitoring capacity. Usually, one detector or sensor monitors one location of a process stream. Multiple sensors are therefore needed to monitor the complete system, adding greatly to the cost of operation. Even with the advent of "smart sensors," silicon chips where all the components are incorporated into a single, inexpensive chip, disadvantages in the multiple sensor requirement remain. While size and cost may be reduced, these sensors are not impervious to poisons such as nitric oxide and service time may be short.

A particular type of detector is disclosed in U.S. Pat. No. 4,834,497 issued to Angel. In Angel's device, chemical substances are detected when they are absorbed onto the coating or cladding of a fiber optic element. To absorb, of course, means to swallow up, to include or take a thing in to the loss of its separate existence, to incorporate. To adsorb means to form a compound upon the adherence of specific liquids or gases in solution to surfaces of materials, usually solids, with which they are in contact. Angel's device is based on the former, absorption.

Several industrial processes generate hydrogen, an explosive gas. Specific limits on the concentration of hydrogen are imposed by law and sound industrial practice to assure occupational safety. Therefore, monitoring of hydrogen concentrations is both appropriate and mandatory.

It is known that hydrogen is weakly adsorbed onto the silica of optical fibers and that this adsorption adversely affects the transmission of data in communication networks. Gaseous molecular hydrogen ($H_2$) itself does not adsorb infrared light, but molecular hydrogen weakly adsorbed on the silica of an optical fiber becomes polarized and actively absorbs infrared radiation. $H_2$, according to the literature, adsorbed on $SiO_2$ forms a weak Si—H bond which has a fundamental vibration of 4.6 micrometers. The absorption of light at 2.42 micrometers is caused by an overtone of the fundamental. The frequency of the absorption band (4132 $cm^{-1}$) is very close to the fundamental vibration (4160 $cm^{-1}$) of gaseous hydrogen. A buffer is commonly applied to the exterior of optical fibers used in the transmission of data and telecommunications to reduce the adsorption of hydrogen and increase the long term use of optical fibers. Without the buffer, the optical fiber adsorbs hydrogen and the increased absorption affects the quality of the signal. A description of this effect is found in "Behavior of Hydrogen Molecules of Silica in Optical Fibers", Mochizuki, et al., IEEE Journal of Quantum Electronics, Vol. QE-20, No. 7, July 1984. It is believed this effect has not heretofore been used for hydrogen detection.

The present invention is directed to overcoming one or more of the problems related to the detection of hydrogen or other substances in a gas.

SUMMARY OF THE INVENTION

This disadvantage of hydrogen adsorbed on silica becomes an advantage in the detection of hydrogen in accordance with the present invention. Furthermore, adsorption of other substances can also affect transmission and can therefore be used to detect their presence.

According to its major aspects, a preferred embodiment of the present invention is an apparatus for detecting the presence of a chemical substance such as hydrogen in a gas. The apparatus comprises a container carrying at least one fiber optic element having a light transmissive core wrapped in a cladding. In the case of hydrogen, molecular hydrogen is adsorbed onto the surface of the fiber optic element. Then near infrared light is passed through the core from a light source connected to one end of the fiber. The light is received by a detecting instrument such as a spectrophotometer at the other end of the fiber. Hydrogen in the gas will be adsorbed onto the cladding and thereby alter the transmissivity of the fiber. The change in transmissivity can be used to infer the presence and amount of hydrogen that was present in the gas. In the case of other chemical substances, the type of cladding will be chosen so that it readily adsorbs that substance thereon, and the light passed through the optic fiber will have a wavelength that is most readily affected by the adsorbed substance.

An important feature of the present invention is the fact that hydrogen is readily desorbed from the cladding. This feature allows the apparatus to be used repeatedly simply by desorbing the hydrogen between each adsorption and measurement. Reversibility of adsorption is optimized in terms of time for desorption by adjusting the core to cladding ratio, the pressure within the container, the temperature of the sensor and the setup of the sensor. The sensor may thus be used repeatedly with a minimum of recovery time. The advantage of reversibility and the speed with which the hydrogen can be desorbed is a major advantage over detectors based on the absorption of substances.

Preferably, the container is connected to process piping so that, by directing a sample of the gas from the process to the container using manual or automatic valves, measurements can be made easily and frequently. Automatic valves are preferred because the valves can be remotely switched and switched faster, a distinct advantage in hazardous or radioactive environments.

Another feature of the present invention is its simplicity. There are no moving parts, the sensor is an optical fiber without the buffer, light passing through the fiber changes as a result of the adsorption of hydrogen from the gas admitted to the container. Yet light measurements can be done very accurately so the sensor can be very sensitive.

A feature of the present invention with respect to hydrogen detection is that the fiber's cladding provides protection against the absorption of sensor poisons such as nitric oxide or water, components in off-gas systems that produce hydrogen.

Still another feature of the present invention is that the measurement can be done quickly in-line with a process system. Samples may then be drawn and measurements made at any time the line is operative. Compared to lab sample testing, results from the present invention can be received much faster, likely only minutes to obtain an accurate reading.

Another feature of the present invention is the ability to monitor more than one point in the process with one detecting system. A sensor may be located at each site of interest and the optical fiber to a multiplexer for sampling the light through each sensor. Alternatively, one sensor can be connected to multiple points in a process stream through by-pass piping and appropriate valving. Monitoring multiple sites nearly simultaneously with limited equipment is a distinct advantage of the present invention.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
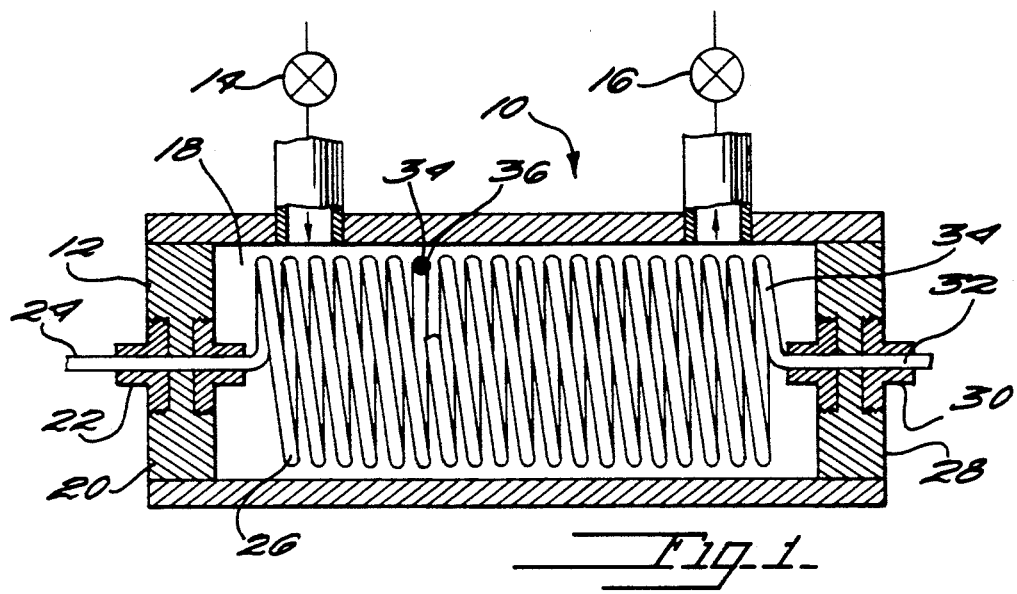
FIG. 1 is a cross sectional view of a fiber optic hydrogen sensor according to a preferred embodiment of the present invention.

Referring now to FIG. 1, the present invention, a hydrogen sensor, is referred to generally by the reference numeral 10. The container 12, made of stainless steel, glass, or other reasonably rigid material that can be sealed, is dimensioned to fit into an industrial process system and may be very small. Container 12 has an intake valve 14 and an outflow valve 16 for controlling the flow of gas from the system into and out of the interior 18 of container 12. Alternatively, if the system itself is sealed, it may serve as the container and no valving is required. Intake valve 12 and outflow valve 14 may be either automatically or manually operated. Automatic valve control mechanisms are preferred for hazardous or radioactive environments because they are easily made remotely operable.

Container 10 has at a first end 20 a fitting 22 which receives an optical fiber 24 from a light source (not shown). Within interior 18 is coiled an optical fiber 26, contiguous with optical fiber 24 and receiving light carried by fiber 24 from the light source. Optical fiber 26 is coiled or convoluted to increase the length of optical fiber 26 within container 10 so there is more surface area exposed to the gas. Optical fiber 26 is preferably a standard silica glass fiber with a doped silica polymer cladding, but without the buffer that is normally applied to the fiber to prohibit hydrogen adsorption. Preferably the core of the fiber has a diameter of approximately 600 microns with a cladding thickness of approximately 20 microns. Coiling of fiber 26 within interior 18 is limited by the radius of curvature of fiber 26 and the dimensions of interior 18.

Container 10 has at a second end 28 a fitting 30 which receives an optical fiber 32, also contiguous with optical fiber 26 and that connects to an instrument (not shown), such as a spectrophotometer, for analysis of the transmitted light. Optical fiber 24 and optical fiber 32 are aligned with opposing ends of fiber 26 so that light transmitted by the light source travels through fibers 24, 26, and 32 to the instrument for analysis.

In use, valves 14 and 16 are opened so that gas to be tested enters interior 18. Valves 14, 16 may be opened for various lengths of time depending on the process system and gas to be tested. Hydrogen present in the gas will be adsorbed onto a cladding 34 covering a core 36 within optical fiber 26. Light in the near infrared spectrum passed along optic fiber 24, through first end 20 and into optic fiber 26 will have increased absorption at wavelengths between approximately 1.24 to 2.42 microns because of the adsorption of hydrogen onto the surface of cladding 34. The light continues out second end 28 into optic fiber 32 and is analyzed by the instrument.

In order to optimize the analysis, the cladding thickness-to-core diameter ratio may be modified, the length of fiber within the container may be increased, a purging gas may be injected between measurements to shorten the time required for desorption, and various other parameters may be altered.

Figure 2:
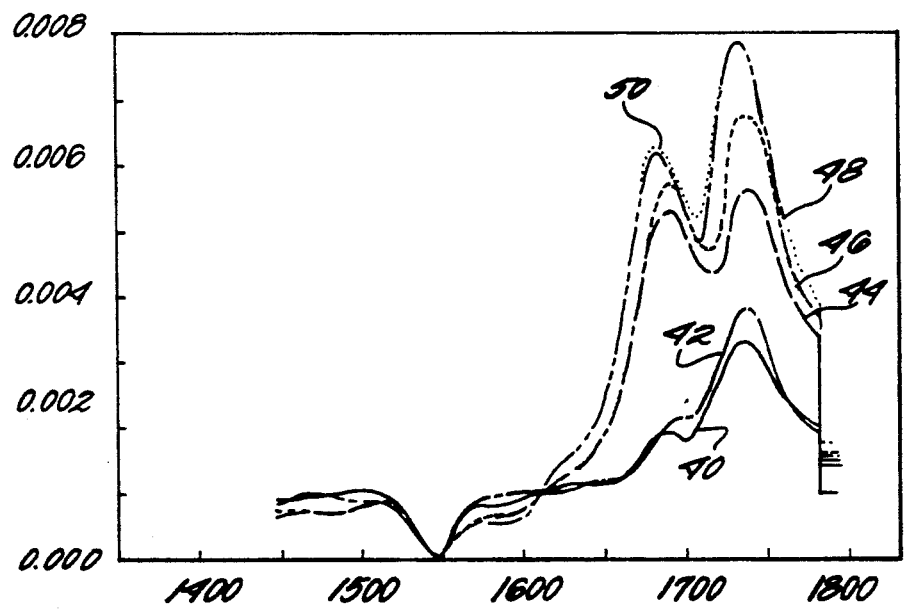
FIG. 2 is a graph of the absorbance of light by a fiber optic sensor with different degrees of adsorbance of hydrogen according to the present invention.

FIG. 2 is a graph depicting the absorbance (Y axis) measured at various wavelengths (X axis) when hydrogen gas at approximately 1 psi is brought into contact with a fiber optic element in a container for various lengths of time. For these measurements, fiber 26 coiled within interior 18 was 7.25 m in length. Curve 40 represents the absorbance at approximately two minutes, curve 42 at four minutes, curve 44 at six minutes, curve 46 at eight minutes, curve 48 at ten minutes, and curve 50 at twelve minutes. Lines 48 and 50 overlapped because the sensor had reached equilibrium in approximately eight minutes.

Figure 3:
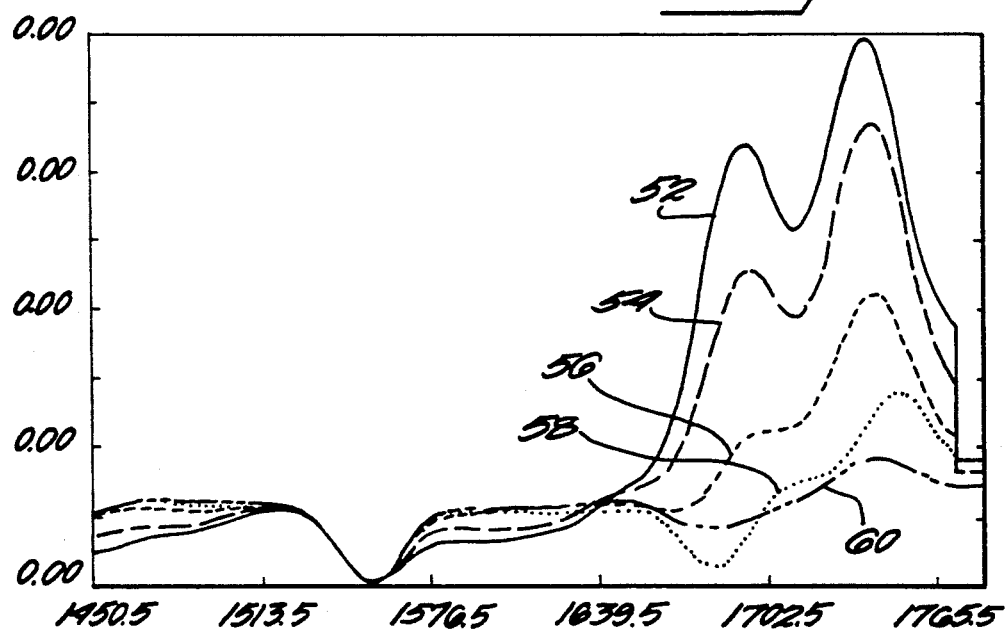
FIG. 3 is a graph of the desorbance of hydrogen from the fiber optic sensor.

FIG. 3 is a graph depicting the absorbance (Y axis) measured at various wavelengths (X axis) at various lengths of time after the hydrogen flow was turned off. Curve 52 represents ten minutes after the hydrogen flow was turned on, curve 54 after fourteen minutes, curve 56 after eighteen minutes, curve 58 after twenty-two minutes, and curve 60 after twenty-four minutes. Times are relative to the time hydrogen was turned on. The hydrogen was turned off after the twelve minute scan. In about 12 minutes after the hydrogen was turned off desorption is complete, that is, the hydrogen adsorption is reversible and the sensor may be used to make a new measurement. Purging the container after the adsorption is complete would reduce the desorption time. If simply the presence of hydrogen was all that needed to be known and not the amount, the adsorption would not have to go to equilibrium.

Figure 4:
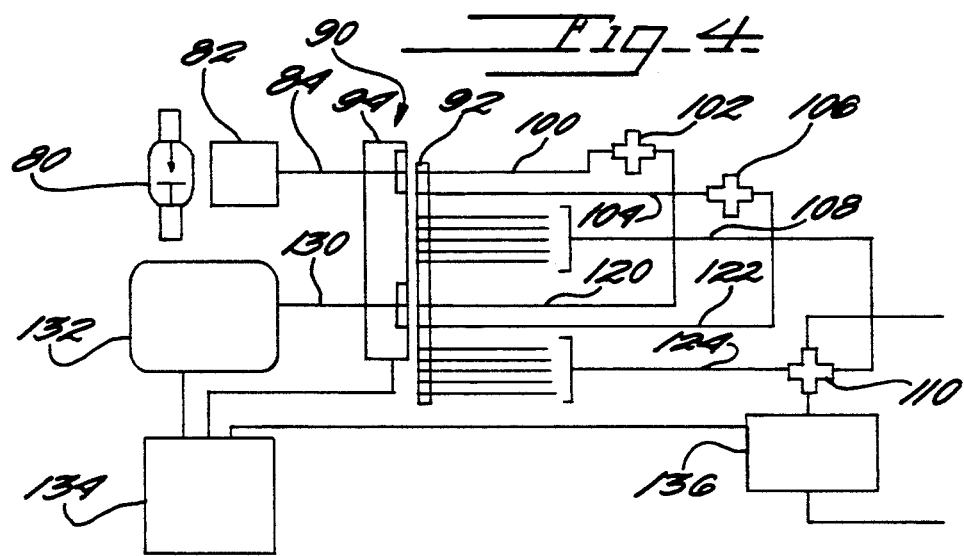
FIG. 4 is a schematic diagram of multi-location, fiber-optic, monitoring system according to a preferred embodiment of the present invention.

Referring now to FIG. 4, a schematic of a system incorporating the present invention is shown. A source of light 80 is collimated by a lens system 82 and directed into an optic fiber 84. Optic fiber 84 carries light from light source 80 through a collimating lens 82 to a multiplexer 90. Multiplexer 90 has two stages, a fixed stage 92 and a moving stage 94, in close proximity to each other. As moving stage 94 moves linearly with respect to fixed stage 92, the end of optic fiber 84 is aligned with one of a series of other optic fibers held in place on fixed stage 92.

One of these optic fibers, 100, leads to a reference cell 102. A second optic fiber 104 attached to fixed stage 92 leads to a standard cell 106. The remainder of optic fibers, collectively, 108, lead to a plurality of hydrogen sensors 110, one at each of the sites to be monitored. Reference cell 102 and standard cell 106 will be described more fully below, however, each returns light in other optic fibers to multiplexer 90 as do hydrogen sensors 110.

Reference cell 102 has a second optic fiber 120 leading to fixed stage 92 of multiplexer 90; standard cell 106 has a second optic fiber 122 leading to multiplexer 90; and hydrogen sensors 110 have a second optic fiber from each, collectively, 124, leading to multiplexer 90. As moving stage 94 moves optic fiber 84 from light source 80, it also moves a third optic fiber 130 into and out of alignment with each of the second optic fibers coming from reference 102, standard 106 and sensors 110. The other end of third optic fiber 130 feeds into a spectrometer 132 which produces a spectrum from the light received. Spectrometer 132 passes spectral data to a computer 134 for analysis. In addition to analysis of spectral data, computer 134 controls the movement of moving stage 94 of multiplexer 90 and directs the actions of a process sampler control 136.

The adsorption onto, rather than absorption of a chemical substance into, the cladding is an important difference between the present invention and other detectors based on optic fibers. Adsorption is much quicker and is much easier to reverse because the chemical substance is only on the surface and not in the cladding. Therefore, measurements can be made much more quickly and more measurements can be made in a given amount of time. Finally, since ordinary silica cladding can be used to adsorb hydrogen, and other light or volatile gases and liquids, there are few if any chemicals that will be absorbed by silica so that light transmissions are not likely to be affected by chemical substances other than those of interest.

It will be apparent to those skilled in the art that many changes and substitutions can be made to the preferred embodiment herein described without departing from the spirit and scope of the present invention which is defined by the appended claims.

What is claimed is:

1. An apparatus for detecting hydrogen for use with a source of light, said apparatus comprising:
   a container in communication with said hydrogen; and
   an optic fiber in said container and in optical communication with said source, said optic fiber having a core and a silica cladding and carrying said light in said core and having a transmissivity, said cladding adsorbing said hydrogen whereby said transmissivity is altered by said adsorbed hydrogen.

2. The apparatus as recited in claim 1, wherein said optic fiber has a first end and a second end, said first end positioned to receive light from outside said container and said second end positioned to transmit light out of said container.

3. The apparatus as recited in claim 1, wherein said light includes near-infrared frequencies.

4. The apparatus as recited in claim 1, wherein said light includes infrared frequencies and said cladding is a silicon polymer.

5. The apparatus as recited in claim 1, further comprising means for controlling the flow of said fluid into and out of said containing means.

6. The apparatus as recited in claim 5, wherein said controlling means is at least one valve.

7. An apparatus for detecting hydrogen, comprising:
   a source of light;
   an optic fiber in optical communication with said source of light, said optic fiber having a silica cladding and a core, said core carrying said light from said source, said optic fiber having a transmissivity, said optic fiber exposed over at least a portion of said optic fiber to said hydrogen so that said hydrogen can be adsorbed thereon; and
   means for measuring a change in said light.

8. The apparatus as recited in claim 7, further comprising a container, said container in communication with said chemical substance and containing said at least a portion of said optic fiber.

9. The apparatus as recited in claim 8, wherein said container further comprises an inlet valve and and outlet valve, said inlet valve admitting said hydrogen and said outlet valve allowing said hydrogen to exit said container.

10. The apparatus as recited in claim 7, wherein said measuring means is a spectrophotometer.

11. An apparatus for detecting chemical substances in a process system, said apparatus comprising:
   at least one source of light;
   a plurality of optic fibers, each optic fiber having a core and a cladding, said optic fibers in optical communication with said at least one source of light, said core carrying light from said at least one source of light and having a transmissivity, said optic fibers exposed over a least a portion of their length to one of said chemical substances;
   multiplexing means for switching from one optic fiber of said plurality of optic fibers to another optic fiber of said plurality of optic fibers; and
   means for measuring a change in said transmissivity in said plurality of optic fibers.

12. The apparatus as recited in claim 11, wherein said chemical substances are hydrogen, said cladding is silica, and said light is infrared, and said measuring means is a spectrophotometer.

13. The apparatus as recited in claim 11, further comprising at least one container having a means for controlling the entrance and exit of one of said chemical substances therefrom, said container in communication with said one of said chemical substances and housing said at least a portion of the length of said at least one optic fiber.

14. A method for determining the concentration of hydrogen, said method comprising the steps of:
  transmitting light from a source of light through a fiber optic element having a core and a silica cladding;
  exposing said optic fiber to said hydrogen so that said hydrogen is adsorbed onto the surface of said cladding; and
  measuring the change in transmissivity of said optic fiber.

15. The method as recited in claim 14, wherein said exposing step further comprises the step of admitting said hydrogen to a container carrying said optical fiber.

16. The method as recited in claim 14, wherein said measuring is by a spectrophotometer.

17. The method as recited in claim 14, wherein said exposing is for a period of less than ten minutes.

18. The method as recited in claim 14, further comprising the steps of:
  stopping the exposure of said hydrogen to said optical fiber; and
  allowing said hydrogen to desorb from said cladding.

* * * * *